(12) United States Patent
Liu et al.

(10) Patent No.: US 9,121,021 B2
(45) Date of Patent: Sep. 1, 2015

(54) REDUCING GALECTIN-12 ACTIVITY TO INFLUENCE THE CELL FUNCTION OF HUMAN SEBOCYTES

(71) Applicant: Academia Sinica, Taipei (TW)

(72) Inventors: Fu-Tong Liu, Taipei (TW); Wei-Chen Hsieh, Taipei (TW); Ri-Yao Yang, Davis, CA (US)

(73) Assignee: ACADEMIA SINICA, Taipei (TW)

( * ) Notice: Subject to any disclaimer, the term of this patent is extended or adjusted under 35 U.S.C. 154(b) by 0 days.

(21) Appl. No.: 14/534,466

(22) Filed: Nov. 6, 2014

(65) Prior Publication Data

US 2015/0126583 A1    May 7, 2015

Related U.S. Application Data

(60) Provisional application No. 61/900,515, filed on Nov. 6, 2013.

(51) Int. Cl.
| | |
|---|---|
| *A61K 48/00* | (2006.01) |
| *C07H 21/02* | (2006.01) |
| *C07H 21/04* | (2006.01) |
| *C12N 15/113* | (2010.01) |

(52) U.S. Cl.
    CPC .......... *C12N 15/113* (2013.01); *C12N 2310/14* (2013.01)

(58) Field of Classification Search
    CPC .............................. A61K 48/00; C12N 15/113
    See application file for complete search history.

(56) References Cited

U.S. PATENT DOCUMENTS

| | | | |
|---|---|---|---|
| 2005/0250123 A1 | 11/2005 | Yang et al. | |
| 2011/0288034 A1* | 11/2011 | Chada et al. | 514/21.2 |

* cited by examiner

*Primary Examiner* — Amy Bowman
(74) *Attorney, Agent, or Firm* — Hsiu-Ming Saunders; Intellectual Property Connections Inc.

(57) ABSTRACT

Methods for the treatment of a disorder characterized by excessive proliferation and/or lipid content of sebocytes are disclosed. In one embodiment of the invention, the method comprises administering to a subject in need thereof a therapeutically effective amount of a pharmaceutical composition comprising a small molecule inhibitor targeted to galectin-12 or a nucleic acid-based inhibitor targeted to galectin-12 and a pharmaceutically acceptable carrier, wherein said inhibitor is a non-naturally occurring molecule and administration of said inhibitor produces a decrease in the proliferation and/or lipid content of the sebocytes. Methods for decreasing sebaceous gland size, inhibiting sebocyte proliferation, and/or inhibiting sebocyte lipid content are also disclosed.

19 Claims, 3 Drawing Sheets

FIG. 1A
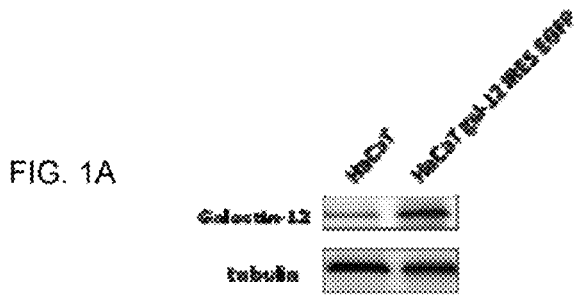
FIG. 1B
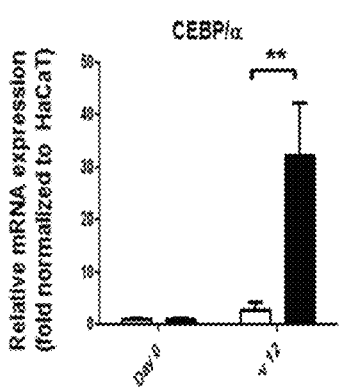
FIG. 1C
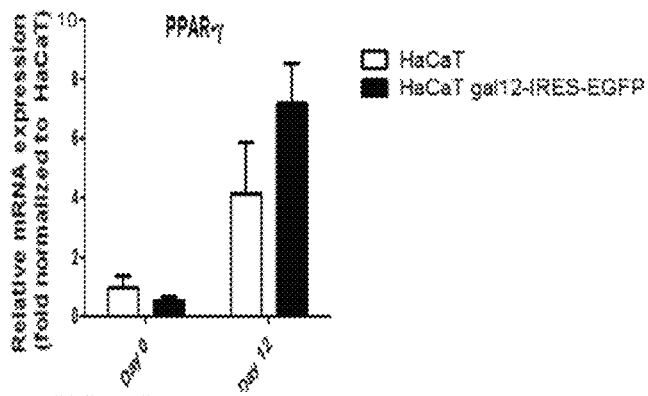
FIG. 1D
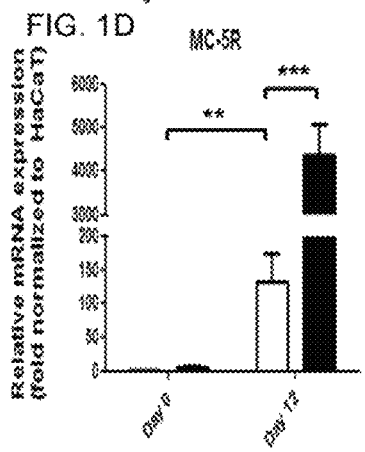
FIG. 1E
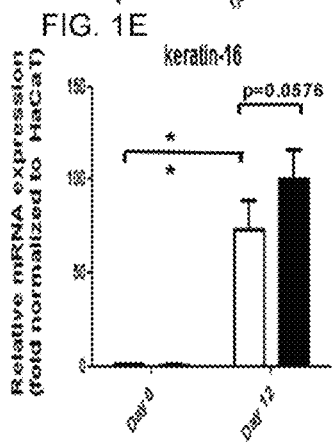
FIG. 2A
siG12_134   sense:      GCAAGAUGGUCAUGCCUGCAAGGAGU (SEQ ID NO: 2);
            antisense:  ACUCCUUGCAGCAUGACCAUCUUGC (SEQ ID NO: 3);
siG12_398   sense:      ACUCCUUGCAGCAUGACCAUCUUGC (SEQ ID NO: 4);
            antisense:  GCAAGAUGGUCAUGCCUGCAAGGAGU (SEQ ID NO: 5);
siG12_490   sense:      UGAUGUUCAGGAAUCCAACAGCCUC (SEQ ID NO: 6);
            antisense:  GAGGUGUUGGAUUCCUGAACAUCA-5` (SEQ ID NO: 7).

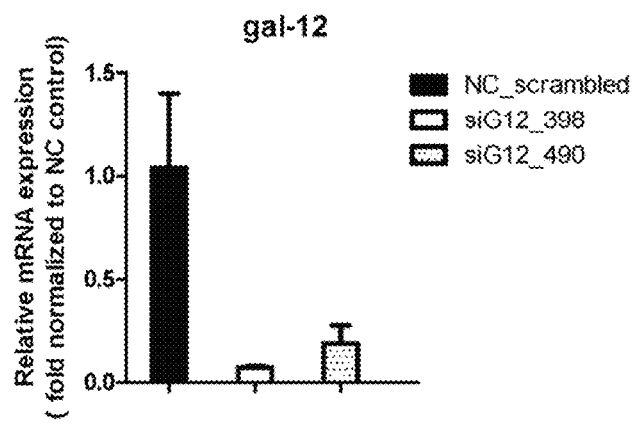
FIG. 2B
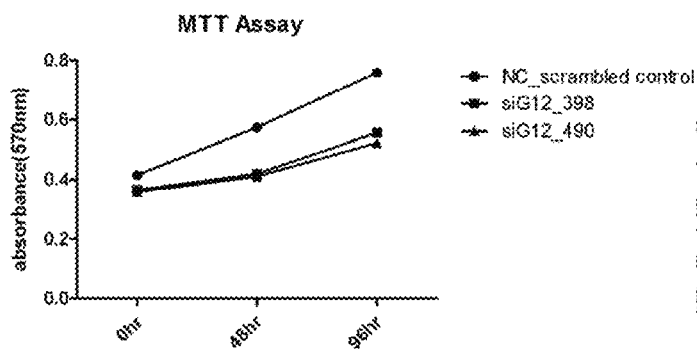
FIG. 3A
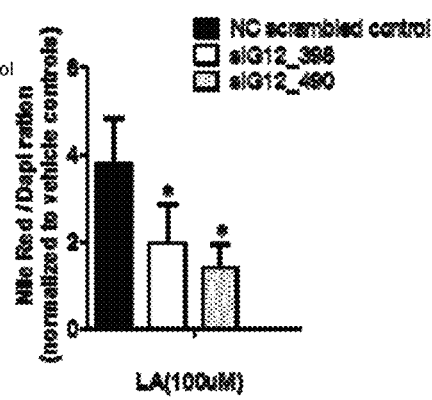
FIG. 3B
FIG. 4A
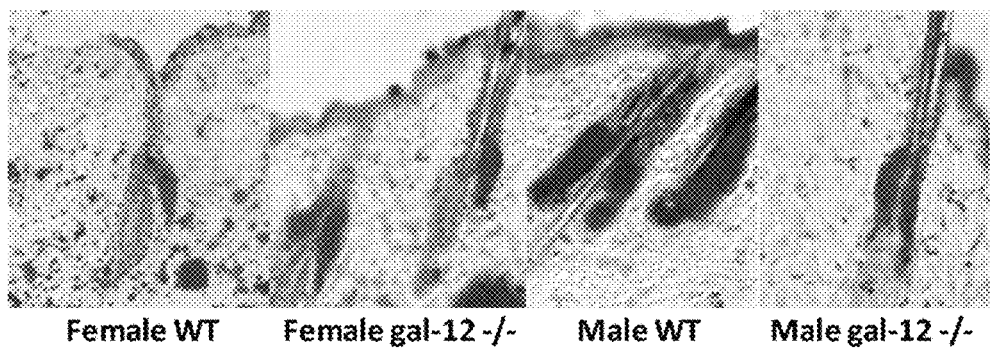

SEQUENCE LISTING

```
<160> NUMBER OF SEQ ID NOS: 7

<210> SEQ ID NO 1
<211> LENGTH: 1347
<212> TYPE: DNA
<213> ORGANISM: Homo sapiens

<400> SEQUENCE: 1
agttggagtt gccccactgt catgtcacct ggagaaaaac tggacccaat tcctgacagc      60
ttcattctgc aaccaccagt cttccacccg gtggttcctt atgtcacgac gatttttgga     120
ggcctgcatg caggcaagat ggtcatgctg caaggagtgg tccctctaga tgcacacagg     180
tttcaggtgg acttccagtg tggctgcagc ctgtgtcccc ggccagatat cgccttccac     240
ttcaaccctc gcttccatac caccaagccc catgtcatct gcaacaccct gcatggtgga     300
cgctggcaaa gggaggcccg gtggccccac ctggccctgc gaagaggctc cagcttcctc     360
atcctctttc tcttcgggaa tgaggaagtg aaggtgagtg tgaatggaca gcactttctc     420
cacttccgct accggctccc actgtctcat gtggacacgc tgggtatatt tggtgacatc     480
ctggtagagg ctgttggatt cctgaacatc aatccatttg tggagggcag cagagagtac     540
ccagctggac atcctttcct gctgatgagc cccaggctgg aggtgccctg ctcacatgct     600
cttccccagg gtctctcgcc tgggcaggtc atcatagtac ggggactggt cttgcaagag     660
ccgaagcatt ttactgtgag cctgagggac caggctgccc atgctcctgt gacactcagg     720
gcctccttcg cagacagaac tctggcctgg atctcccgct gggggcagaa gaaactgatc     780
tcagccccct tcctctttta cccccagaga ttctttgagg tgctgctcct gttccaggag     840
ggagggctga agctggcgct caatgggcag gggctggggg ccaccagcat gaaccagcag     900
gccctggagc agctgcggga gctccggatc agtggaagtg tccagctcta ctgtgtccac     960
tcctgaggat ggttccaggg aaataccgcc agaaaacaag aaggtcagcc cactcccagg    1020
gccccactct cctcccctca ttaaaccatc cacctgacac cagcacatca ggcctggttc    1080
acctctgggg tcacgagact gagtctacag gagctttggg cctgagggaa ggcacaagag    1140
tgcaaaggtt cctcgaactc tgcaccttcc tccaccagga gcctgggata tggctccatc    1200
tgccttcagg gcctggactg cactcacaga ggcaagtgtt gtagactaac aaagatactc    1260
```

-continued

```
caaaatacaa tggcttaaag aatgtggtca tttattcttt attatttatt tatttgtggt    1320
caaataaata aataaggtta tttattt                                        1347
```

<210> SEQ ID NO 2
<211> LENGTH: 26
<212> TYPE: DNA
<213> ORGANISM: Artificial Sequence
<220> FEATURE:
<223> OTHER INFORMATION: siG12_134 sense

<400> SEQUENCE: 2

```
gcaagauggu caugccugca aggagu                                           26
```

<210> SEQ ID NO 3
<211> LENGTH: 25
<212> TYPE: DNA
<213> ORGANISM: Artificial Sequence
<220> FEATURE:
<223> OTHER INFORMATION: siG12_134 antisense

<400> SEQUENCE: 3

```
acuccuugca gcaugaccau cuugc                                            25
```

<210> SEQ ID NO 4
<211> LENGTH: 25
<212> TYPE: DNA
<213> ORGANISM: Artificial Sequence
<220> FEATURE:
<223> OTHER INFORMATION: siG12_398 sense

<400> SEQUENCE: 4

```
acuccuugca gcaugaccau cuugc                                            25
```

<210> SEQ ID NO 5
<211> LENGTH: 25
<212> TYPE: DNA
<213> ORGANISM: Artificial Sequence
<220> FEATURE:
<223> OTHER INFORMATION: siG12_398 antisense

<400> SEQUENCE: 5

```
gcaagauggu caugcugcaa ggagu                                            25
```

<210> SEQ ID NO 6
<211> LENGTH: 25
<212> TYPE: DNA
<213> ORGANISM: Artificial Sequence
<220> FEATURE:
<223> OTHER INFORMATION: siG12_490 sense

<400> SEQUENCE: 6

```
ugauguucag gaauccaaca gccuc                                            25
```

<210> SEQ ID NO 7
<211> LENGTH: 24
<212> TYPE: DNA
<213> ORGANISM: Artificial Sequence
<220> FEATURE:
<223> OTHER INFORMATION: siG12_490 antisense

<400> SEQUENCE: 7

```
gagguguugg auuccugaac auca                                             24
```

REDUCING GALECTIN-12 ACTIVITY TO INFLUENCE THE CELL FUNCTION OF HUMAN SEBOCYTES

REFERENCE TO RELATED APPLICATION

The present application claims the priority to U.S. Provisional Application Ser. No. 61/900,515, filed Nov. 6, 2013, which is herein incorporated by reference in its entirety.

FIELD OF THE INVENTION

The present invention relates generally to galectin, and more specifically to galectin-12.

BACKGROUND OF THE INVENTION

Deregulation of sebaceous gland, including enhanced sebocyte proliferation and sebum production, with abnormal differentiation and lipogenesis, is associated with several human diseases such as acne vulgaris, sebaceous hyperplasia, and sebaceous gland carcinoma, atopic dermatitis, seborrheic dermatitis and primary cicatricial alopecia. A mechanistic understanding of sebocyte proliferation and differentiation is important for developing novel therapeutic strategies to manage certain sebaceous gland disorder.

Acne vulgaris, the most common sebaceous gland diseases, is still a challenge to dermatologists since most medical and surgical therapies developed so far to treat acne vulgaris have relatively modest efficacy, possibly because of the inherent pathological complexity of the disease. Currently, topical retinoids, oral isotretinoin, and antimicrobials have been widely used as first-line therapies for acne since they can suppress sebaceous gland activity such as suppressing sebum secretion and reducing sebaceous lipogenesis or reduce the colonization of *P. Acnes* and its subsequent pro-inflammatory effects on comedogenesis. Unfortunately, these conventional therapies may not be effective against refractory acne, can lead to antibiotic resistance, or are associated with serious side effects. Although light and laser therapy and photodynamic therapy are growing in popularity as adjunctive treatments, it usually only shows short-term efficacy for inflammatory acne vulgaris. Therefore, their use as alternative acne treatments cannot be recommended until long-term studies are available that rule out a potential irreversible sebaceous gland destruction.

Galectin-12, a member of a β-galactoside-binding lectin family, contains two carbohydrate recognition domains (CRDs). Its mRNA contains five AU-rich motifs (AUUUA) which are known to confer instability to mRNA in the 3'-untranslated region, might therefore contributing to very restrict expression in adipocytes and peripheral blood leucocytes. (Yang, R. Y. et al., J Biol. Chem. 276:20252-20260 (2001)). Galectin-12 plays an important role in modulating adipogenesis by positively regulating expression of CCAAT enhancer-binding protein (C/EBP) and peroxisome proliferator-activated receptor (PPAR). (Yang, R. Y. et al., J Biol Chem. 279(28):29761-6. (2004) In addition, galectin-12 is specifically localized on lipid droplet and negatively regulates lipolysis and insulin sensitivity. (Yang, R. Y. et al., Proc Natl Acad Sci. 15; 108(46):18696-701(2011). Both C/EBPs and PPARs are also expressed in sebaceous gland cells and regulate sebocyte lipogenesis and differentiation. It has been demonstrated that galectin-12 is also expressed in human sebaceous glands and cultured sebocytes. (Harrison, W. J. et al., J Invest Dermatol. 127(6):1309-17. (2007)). However, its roles in sebocyte differentiation and the pathophysiology of sebaceous gland disorders remain to be elucidated.

SUMMARY OF THE INVENTION

In one aspect, the invention relates to a method for the treatment of a disorder characterized by excessive proliferation and/or lipid content of sebocytes. The method comprises the step of administering to a subject in need thereof a therapeutically effective amount of a pharmaceutical composition comprising:

(a) a non-naturally occurring small molecule inhibitor of galectin-12, or a non-naturally occurring nucleic acid-based inhibitor molecule targeted to galectin-12; and (b) a pharmaceutically acceptable carrier, wherein administration of said inhibitor produces a decrease in the proliferation and/or lipid content of sebocytes.

In one embodiment of the invention, the nucleic acid-based inhibitor targeted to galectin-12 is selected from the group consisting of small interfering RNAs (siRNAs), galectin-12 aptamers, and modified galectin-12 siRNAs, short hairpin RNA, and ribozymes.

In another embodiment of the invention, the nucleic acid-based inhibitor is a small interfering RNA (siRNA).

In another embodiment of the invention, the siRNA comprises a sense RNA strand and an antisense RNA strand, wherein the sense and the antisense RNA strands form an RNA duplex, and wherein the sense RNA strand comprises a nucleotide sequence substantially identical to human galectin-12 mRNA sequence (SEQ ID NO: 1).

In another embodiment of the invention, the sense RNA strand comprises a sequence selected from the group consisting of SEQ ID NOs: 2, 4, and 6.

In another embodiment of the invention, the antisense RNA strand comprises a sequence selected from the group consisting of SEQ ID NOs: 3, 5, and 7.

In another embodiment of the invention, the sense RNA strand consists of a sequence selected from the group consisting of SEQ ID NOs: 2, 4, and 6.

In another embodiment of the invention, the anti sense RNA strand consists of a sequence selected from the group consisting of SEQ ID NOs: 3, 5, and 7.

In another embodiment of the invention, the subject is a human patient afflicted with acne or a sebaceous gland disorder, or both.

In another embodiment of the invention, said pharmaceutical composition is formulated for oral, topical, intravenous, intramuscular or subcutaneous administration.

In another embodiment of the invention, the sebaceous gland disorder is selected from the group consisting of sebaceous hyperplasia, sebaceous gland carcinoma, atopic dermatitis, seborrheic dermatitis and primary cicatricial alopeci.

In another aspect, the invention relates to a method for inhibiting proliferation and/or lipid content of sebocytes. The method comprises the step of contacting the sebocytes in a sebaceous gland with a therapeutically effective amount of a pharmaceutical composition comprising:

(a) a non-naturally occurring small interfering RNA (siRNA), or a non-naturally occurring antisense RNA, specifically directed to a galectin-12 nucleic acid; and (b) a pharmaceutically acceptable carrier.

In one embodiment of the invention the sebocytes are present in a human patient.

Further in another aspect, the invention relates to a method for decreasing sebaceous gland size, inhibiting sebocyte proliferation, and/or inhibiting sebocyte lipid content. The method comprises:

administering to a subject in need thereof a therapeutically effective amount of a pharmaceutical composition comprising:
(a) a non-naturally occurring small molecule inhibitor of galectin-12, or a non-naturally occurring nucleic acid-based inhibitor molecule targeted to human galectin-12 mRNA; and
(b) a pharmaceutically acceptable carrier,
wherein administration of said inhibitor produces a decrease in the sebaceous gland size, sebocyte proliferation, and/or sebocyte lipid content.

In one embodiment of the invention, wherein the subject is a male.

In another embodiment of the invention, the subject is a human patient afflicted with acne or a sebaceous gland disorder, or both.

In another embodiment of the invention, the sebaceous gland disorder is selected from the group consisting of sebaceous hyperplasia, sebaceous gland carcinoma, atopic dermatitis, seborrheic dermatitis and primary cicatricial alopeci.

In another embodiment of the invention, the nucleic acid-based inhibitor targeted to human galectin-12 mRNA is selected from the group consisting of small interfering RNAs (siRNAs), galectin-12 aptamers, and modified galectin-12 siRNAs, short hairpin RNA, and ribozymes.

In another embodiment of the invention, the siRNA comprises a sense RNA strand and an antisense RNA strand, wherein the sense and the antisense RNA strands form an RNA duplex, and wherein the sense RNA strand comprises a nucleotide sequence substantially identical to a target sequence of about 19 to about 28 continuous nucleotides in human galectin-12 mRNA sequence (SEQ ID NO: 1).

In another embodiment of the invention, the target sequence comprises a sequence selected from the group consisting of SEQ ID NOs: 2, 4, and 6. The siRNA inhibits the activity and/or expression of galectin-12 protein in the sebocytes.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIGS. 1A-E show overexpression of galectin-12 in human HaCaT keratinocytes was associated with a sebocyte-like differentiation pattern. (A) Western blotting showing the increased galectin-12 protein levels in HaCaT transfected with gal-12 overexpression vector (gal12-IRES-EGFP). (B-E) Both parental HaCaT cells and HaCaT cells transfected with gal12-1RES-EGFP were treated with 10 nM EGF, 10 nM insulin, 1 μM troglitazone (PPAR-γ agonists) and 100 Mm WY14643(PPAR activator) for 12 days. Gene expression for gal-12, adipogenic factors (CEBP/α and PPAR-γ), and mature sebocyte markers (MC-5R and K16) was analyzed after 12 days of differentiation.

FIGS. 2A-B show down-regulation of endogenous galectin-12 expression in human SEB-1 sebocytes. (A) Sequences of siRNAs used in the experiments. (B) Real-time PCR showing the decreased galectin-12 mRNA levels 2 days after transfection with galectin-12 siRNAs.

FIGS. 3A-B show down-regulation of galectin-12 in human sebocytes reduced their proliferation and lipogenesis. (A) Cell proliferation assay was measured in sebocytes transfected with negative scrambled control, gal-12 siRNA_398, 490 by MTT assay at 0, 48, and 96 hr. (B) Lipid content was measured in sebocytes transfectants treated with 100 μM linoleic acid (LA) for 48 hr using ADIPORED™.

FIGS. 4A-C show the sebaceous gland size in male Lgals12−/− mice was reduced compared with that of male littermate controls (A) Oil Red O staining for intracellular lipids in male/female wild type littermates and gal-12 null mice. (B) Quantification of sebaceous gland in male/female wild type littermates and gal-12 null mice. n>25 sebaceous glands from mice for each genotype. (C) Quantification of sebaceous gland in male wild type littermates and gal-12 null mice. (n=6, p=0.0003)

DETAILED DESCRIPTION OF THE INVENTION

Figure 4B:
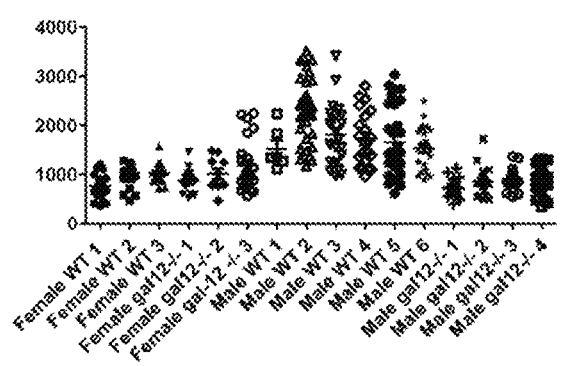

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

DEFINITIONS

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The terms "small interfering RNA (siRNA)", "short interfering RNA or silencing RNA" and "silencing RNA" are interchangeable. siRNA is a class of double-stranded RNA molecules. siRNA plays many roles, but its most notable is in the RNA interference (RNAi) pathway, where it interferes with the expression of specific genes with complementary nucleotide sequence.

As used herein, a nucleic acid sequence "substantially identical" to a target sequence contained within the target mRNA is a nucleic acid sequence which is identical to the target sequence, or which differs from the target sequence by one or more nucleotides. Sense strands of the invention which comprise nucleic acid sequences substantially identical to a target sequence are characterized in that siRNA comprising such sense strands induce RNAi-mediated degradation of mRNA containing the target sequence. For example, an siRNA of the invention can comprise a sense strand comprise nucleic acid sequences which differ from a target sequence by one, two or three or more nucleotides, as long as RNAi-mediated degradation of the target mRNA is induced by the siRNA.

The sense and antisense strands of the present siRNA can comprise two complementary, single-stranded RNA molecules or can comprise a single molecule in which two complementary portions are base-paired and are covalently linked by a single-stranded "hairpin" area. Without wishing to be bound by any theory, it is believed that the hairpin area of the latter type of siRNA molecule is cleaved intracellularly by the "Dicer" protein (or its equivalent) to form an siRNA of two individual base-paired RNA molecules (see Tuschl, T. (2002), supra). As described below, the siRNA can also contain alterations, substitutions or modifications of one or more ribonucleotide bases. For example, the present siRNA can be altered, substituted or modified to contain one or more deoxyribonucleotide bases.

Methods of making and use of siRNA are well-known in the art. For example, US20050250123 A1 disclose making and using siRNAs that are designed to target to galectin-12 mRNA, the content of which is incorporated herein by reference in its entirety.

Methods of making and use of modified siRNA molecules are well-known in the art. For example, U.S. Pat. Nos. 7,915,399, 8,101,741, 8,188,263, 8,513,403 disclose modified siRNA and use thereof, the content of which are all incorporated herein by reference in their entireties.

Aptamers are oligonucleic acid or peptide molecules that bind to a specific target molecule. Aptamers can be combined with ribozymes to self-cleave in the presence of their target molecule. Aptamers can be classified as DNA or RNA or XNA aptamers. They consist of (usually short) stands of oligonucleotides. Peptide aptamers. They consists of a short variable peptide domain attached at both ends to a protein scaffold.

Making and use of aptamers are well known in the art. For example, U.S. Pat. No. 8,552,166 discloses High-affinity nucleic acid aptamers against sclerostin protein; U.S. Pat. No. 8,569,252 discloses Nucleolin specific aptamer and use thereof, U.S. Pat. No. 8,569,065 discloses RNA aptamer; U.S. Pat. No. 8,552,167 discloses aptamer-nucleic acid nanostructures for treating tumors in a mammal, U.S. Pat. No. 8,541,561 discloses DNA aptamer, the content of which are all incorporated herein by reference in their entireties.

A significant progress has been made in targeted delivery of siRNA in vivo for therapeutic applications (Sabrina Oliveira et al. "Targeted Delivery of siRNA" Journal of Biomedicine and Biotechnology, Volume 2006, Article ID 63675, Pages 1-9, the content of which is incorporated herein by reference in its entirety).

Ribozymes can also function as inhibitors of galectin-12 expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of galectin-12 mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable.

```
galectin-12 mRNA sequence: (SEQ ID NO: 1);
siG12_134
sense:
                                        (SEQ ID NO: 2)
GCAAGAUGGUCAUGCCUGCAAGGAGU;

antisense:
                                        (SEQ ID NO: 3)
ACUCCUGCAGCAUGACCAUCUUGC;

siG-12_398
sense:
                                        (SEQ ID NO: 4)
ACUCCUUGCAGCAUGACCAUCUUGC;

antisense:
                                        (SEQ ID NO: 5)
GCAAGAUGGUCAUGCUGCAAGGAGU;

siG12_490
sense:
                                        (SEQ ID NO: 6)
UGAUGUUCAGGAAUCCAACAGCCUC;

antisense:
                                        (SEQ ID NO: 7)
GAGGUGUUGGGAUUCCUGAACAUCA-5'.
```

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Methods

Cell Culture.

The SEB-1 human sebocyte cell line was kindly provided by Dr. Thiboutot and was cultured in Dulbecco's modified Eagle's medium (DMEM)/Ham's F-12 3:1, fetal bovine serum 5%, adenine $1.8 \times 10^{-4}$ M, hydrocortisone 0.4 µg per ml, insulin 5 µg per ml, epidermal growth factor 10 ng per ml, cholera toxin $1.2 \times 10^{-10}$ M, and antibiotics (100×). HaCaT cells was cultured in DMEM medium with 10% FBS, in a 37° C. incubator with 10% $CO_2$.

Induction of HaCaT Differentiation into Sebocyte-Like Cells

Gal12-IRES-EGFP and empty vector control were transfected into HaCaT cells and cells were selected by 10 µg/ml gentamicin. HaCaT cells were plated at a density of 20-25,000 cells/cm$^2$ and allowed to attach overnight in sebocyte media (DMEM and Ham F-12 (1:1), 6% FBS, P/S, and EGF (10 nM). Cells were induced for sebocyte differentiation with sebocyte differentiation media containing 10 nM insulin, 1 µM troglitazone, 100 µM WY14643, and 10 nM dihydroxytestasterone in sebocyte media for 12 days. Gene expression for gal-12, adipogenic factors (CEBP/α and PPAR-γ), and mature sebocyte markers (MC-5R and K16) was analyzed after 12 days of differentiation.

RNA Interference with Small Interfering RNA (siRNA).

The transfection of SEB-1 cells with siRNAs was performed using lipofectamine. Briefly, one day prior to transfection, approximately $1 \times 10^4$ cells were seeded in wells of 24 well plates so that they would be ~50% confluent the following day. Cells on each well were transfected with 2 µl Lipofectamine and 40 nM siRNA. One day after transfection, transfection mixture was removed and 4 ml fresh culture medium was added. After 2 days of transfection, cells were treated with 100 µM linoleic acid for 24 hours to induce lipid synthesis in SEB-1 cells.

MTT Cell Proliferation Assay.

Cells were plated ($2.5 \times 10^3$ cells/well) in replicates of 6 in 96-well culture plates and transfected with scrambled control or siG12 siRNAs for 48 or 96 hours. To measure the cell proliferation, 20 µL of 5 mg/mL MTT (Sigma) was added into each well and assayed using standard methodology.

Measure of lipid content using Nile red 4',6-diamidino-2-phenylindole (DAPI) staining.

After 24 hours of 100 uM linoleic acid treatment, the level of lipid content was determined with the use of a luminescent plate reader. The medium was removed; wells were washed twice with PBS and fixed with 200 µL of 4% PFA for 30 min at RT. Subsequently, wells were washed twice with PBS and the background fluorescence was read in 200 µL of PBS with the use of DAPI (355/460) and Nile red (485/540) filter sets as per the manufacturer's instructions. These filter sets were used because they provided the closest match to DAPI (excitation at 358 nm and emission at 461 nm) and Nile red (excitation at 450-500 nm and emission at >528 nm). After background reading, the PBS was removed and 200 µL of saponin (0.2% w/v in PBS) was added along with DAPI (INVITROGEN™) at a final concentration of 1 µg·mL$^{-1}$ and Nile red at a final concentration of 1 µg·mL$^{-1}$. The plate was then wrapped in foil and incubated at RT for 15 minutes. After three washes with PBS, 200 µL of PBS was added and plates were again read as above.

To calculate the Nile red:DAPI ratio, the background fluorescence was first subtracted from the readings. The mean fluorescent reading for six replicates was calculated for both Nile red and DAPI; Nile red:DAPI ratio was then established and normalized to vehicle treated cells.

Histology and Immunofluorescence.

Skins were embedded in OCT, frozen, sectioned, and fixed in 4% formaldehyde. For paraffin sections, skins were incubated in 4% formaldehyde at 4° C. overnight, dehydrated with a series of increasing concentrations of ethanol and xylene, and embedded in paraffin. Paraffin sections were rehydrated in decreasing concentrations of ethanol and subjected to antigen unmasking in 10 mM Citrate, pH 6.0. Sections were subjected to immunofluorescence microscopy as described. Oil red O (ORO) staining was performed by incubating skin samples in 0.18% ORO for 10 min, washing with PBS, and counterstaining with hematoxylin.

Sebaceous Gland Area Measurements.

To analyze sebaceous glands, skin tissue was stained with ORO, mounted, and analyzed. Individual gland size was quantified using morphometric measurements with Image J software. n>25 sebaceous glands from mice for each genotype. Quantitation of Ki67+ve cells were determined from at least ten 10× images of H&E-stained tissue sections per mouse. Statistical analysis was performed using the unpaired Student's t test.

Results

This invention relates to the findings of overexpression of galectin-12 in human HaCaT keratinocytes and the discovery that galectin-12 was highly up-regulated when HaCaT cells differentiated into sebocytes (15-fold, p=0.0017). Overexpression of galectin-12 in HaCaT keratinocytes induced a gene expression profile consistent with sebocyte-like differentiation (FIGS. 1A-B), which indicates that modulation of galectin-12 expression regulates sebocyte differentiation.

This invention further relates to short interfering RNAs (siRNAs) for use in inhibiting expression of galectin-12 and its consequent activity (FIGS. 2A-B). The invention also provides use of galectin-12 siRNAs for inhibiting human sebocyte proliferation and lipid synthesis. Knock-down of galectin-12 in SEB-1 sebocytes reduced their proliferation (−29.5%, p=0.01) and lipogenesis (−63.3%, p=0.0118) (FIGS. 3A-B). This finding demonstrates that inhibiting expression of galectin-12 by siRNA can reduce sebocyte proliferation and lipogenesis.

Figure 4C:
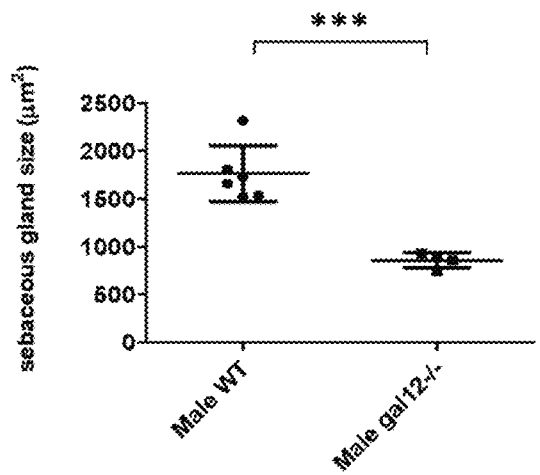
Figure 4D:
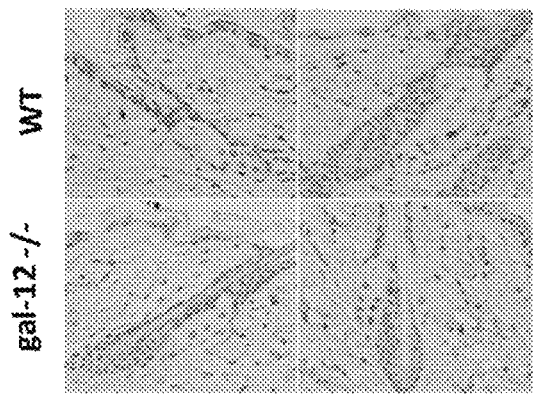
FIGS. 4D-E show less ki67+ proliferating cells in Lgals12−/− mice, compared to the WT mice. (D) Ki67 staining for proliferation cells in male Lgals12−/− mice and their littermate controls. (E). Quantification of ki67 positive cells in each sebaceous gland in male Lgals12−/− mice and their littermate controls n>25 sebaceous glands from mice for each genotype (n=5, p=0.0286).
Figure 4E:
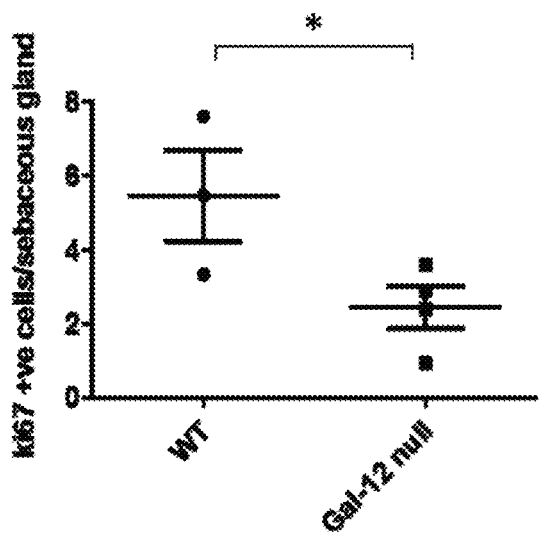

The invention also demonstrates that male galectin-12 null mice have smaller sebaceous glands, compared to male WT mice, (854.1 µm$^2$ versus 1759 µm$^2$, p=0.0003, n=6). In addition, galectin-12 ablation reduced sebocyte proliferation in vivo. These data suggest that the size of sebaceous glands and sebocyte proliferation can be reduced by inhibition of galectin-12 activity or expression (FIGS. 4A-C). The finding has important implications in treatment of acne and other sebaceous gland disorders.

Taken together, this invention demonstrates that galectin-12 modulates several key sebaceous functions, including sebocyte differentiation, proliferation and lipogenesis. The results suggest that galectin-12 may be a novel target for modulating sebaceous functions and for the treatment of acne and sebaceous glands disorders. In addition, this invention also indicates that galectin-12 is expressed specifically in sebaceous gland but not expressed in dermis and other skin cells, therefore indicating a great potential and a distinct advantage of developing galectin-12 inhibitors such as modified siRNAs as a therapeutic tool for the treatment of acne. It is easy to modulate the expression of galectin-12 by inhibitors without targeting other skin cells. Thus, it is possible to develop galectin-12 inhibitors, galectin-12 antagonists, and galectin-2 antisense oligonucleotides, etc. as therapeutic drugs for acne and other sebaceous glands diseases such as sebaceous hyperplasia, and sebaceous gland carcinoma, atopic dermatitis, seborrheic dermatitis and primary cicatricial alopeci. The invention also relates to galectin-12 aptamers and modified galectin-12 siRNAs to target galectin-12 in human sebocytes, which can be applied in clinical therapy.

The foregoing description of the exemplary embodiments of the invention has been presented only for the purposes of illustration and description and is not intended to be exhaustive or to limit the invention to the precise forms disclosed. Many modifications and variations are possible in light of the above teaching. The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A method for the treatment of acne or a sebaceous gland disorder, or both, comprising:
   administering to a subject in need of treating the acne or sebaceous gland disorder, or both a therapeutically effective amount of a pharmaceutical composition comprising:
   (a) a non-naturally occurring, small molecule inhibitor of galectin-12, or a non-naturally occurring nucleic acid-based inhibitor targeted to galectin-12; and
   (b) a pharmaceutically acceptable carrier,
   wherein the sebaceous gland disorder is selected from the group consisting of sebaceous hyperplasia, sebaceous gland carcinoma, atopic dermatitis, seborrheic dermatitis and primary cicatricial alopeci.

2. The method of claim 1, wherein the nucleic acid-based inhibitor targeted to galectin-12 is selected from the group consisting of small interfering RNAs (siRNAs), galectin-12 aptamers, and modified galectin-12 siRNAs, short hairpin RNA, and ribozymes.

3. The method of claim 2, wherein the nucleic acid-based inhibitor is a small interfering RNA (siRNA).

4. The method of claim 3, wherein the siRNA comprises a sense RNA strand and an antisense RNA strand, wherein the sense and the antisense RNA strands form an RNA duplex, and wherein the sense RNA strand comprises a nucleotide sequence substantially identical to human galectin-12 in RNA sequence (SEQ ID NO: 1).

5. The method of claim 3, wherein the sense RNA strand comprises a sequence selected from the group consisting of SEQ NOs: 2, 4, and 6.

6. The method of claim 3, wherein the antisense RNA strand comprises a sequence selected from the group consisting of SEQ ID NOs: 3, 5, and 7.

7. The method of claim 3, wherein the antisense RNA strand consists of a sequence selected from the group consisting of SEQ ID NOs: 3, 5, and 7.

8. The method of claim 1, wherein the subject is a human patient afflicted with the sebaceous gland disorder.

9. The method of claim 8, wherein the subject is afflicted with the sebaceous hyperplasia.

10. The method of claim 1, wherein said pharmaceutical composition is formulated for oral, topical, intravenous, intramuscular, or subcutaneous administration.

11. A method for inhibiting proliferation and/or lipid content of sebocytes, comprising:
    contacting the sebocytes with a therapeutically effective amount of a pharmaceutical composition comprising:
    (a) a non-naturally occurring small interfering RNA (siRNA), or a non-naturally occurring antisense RNA, specifically directed to a galectin-12 nucleic acid; and
    (b) a pharmaceutically acceptable carrier,
    wherein the siRNA comprises a sense RNA strand and an antisense RNA strand, the sense and the antisense RNA strands forming an RNA duplex, and wherein the sense RNA strand compares a nucleotide sequence substantially identical to a target sequence of about 19 to about 28 continuous nucleotides in human galectin-12 mRNA sequence (SEQ ID NO: 1), and the sense RNA strand comprises a sequence selected from the group consisting of SEQ ID NOs: 2, 4, and 6.

12. The method of claim 11, wherein the sebocytes are present in a human patient.

13. The method of claim 11, wherein the antisense RNA strand comprises a sequence selected from the group consisting of SEQ ID NOs: 3, 5, and 7.

14. A method for decreasing sebaceous gland size, comprising:
    administering to a subject in need thereof a therapeutically effective amount of a pharmaceutical composition comprising:
    (a) a non-naturally occurring small molecule inhibitor of galectin-12, or a non-naturally occurring nucleic acid-based inhibitor targeted to human galectin-12 mRNA; and
    (h) a pharmaceutically acceptable carrier,
    wherein the subject is a male.

15. The method of claim 14, wherein the subject is a human patient afflicted with acne of a sebaceous gland disorder, or both.

16. The method of claim 15, wherein the sebaceous gland disorder is selected from the group consisting of sebaceous hyperplasia, sebaceous gland carcinoma, atopic dermatitis, seborrheic dermatitis and primary cicatricial alopeci.

17. The method of claim 15, wherein the nucleic acid-based inhibitor targeted to human galectin-12 mRNA is selected from the group consisting of small interfering RNAs (siRNAs), galectin-12 aptamers, and modified galectin-12 siRNAs, short hairpin RNA, and ribozymes.

18. The method of claim 14, wherein the siRNA comprises a sense RNA strand and an antisense RNA strand, wherein the sense and the antisense RNA strands form an RNA duplex, and wherein the sense RNA strand comprises a nucleotide sequence substantially identical to a target sequence of about 19 to about 28 continuous nucleotides in human galectin-12 mRNA sequence (SEQ ID NO: 1).

19. The method of claim 14, wherein the target sequence comprises a sequence selected from the group consisting of SEQ ID NOs: 2, 4, and 6.

* * * * *